Figure 1:
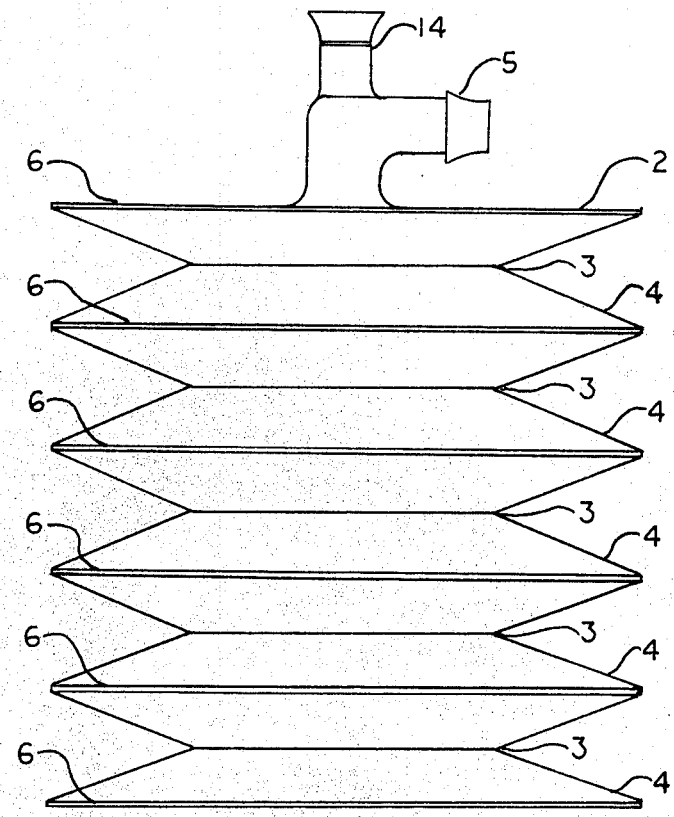
Figure 2:
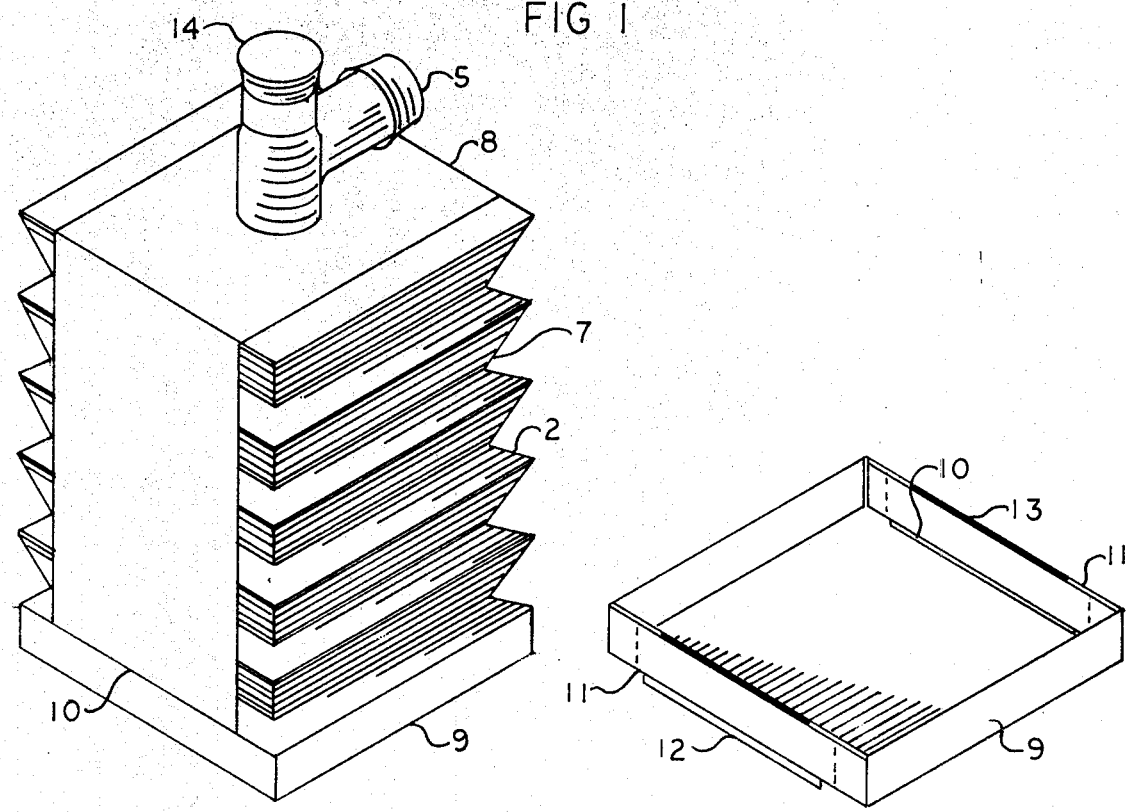
Figure 3:
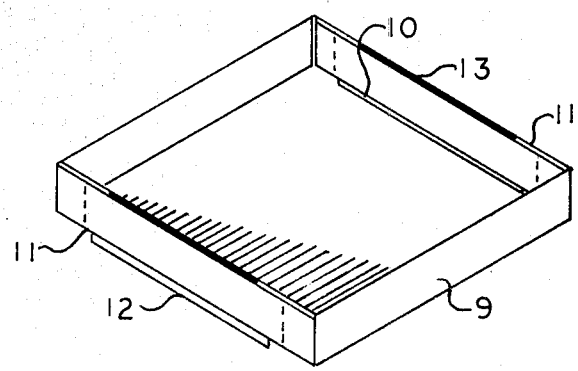

United States Patent [19]

Gereg

[11] 4,345,605
[45] Aug. 24, 1982

[54] LUNG EXERCISER

[76] Inventor: Gordon A. Gereg, 557-A Blue Church Rd., Coopersburg, Pa. 18036

[21] Appl. No.: 199,084

[22] Filed: Oct. 20, 1980

[51] Int. Cl.³ .................. A61B 5/08; A63B 23/00; F16J 3/00
[52] U.S. Cl. ........................... 128/728; 272/99; 92/43; 73/262; 128/205.17
[58] Field of Search ............ 128/725, 727, 728, 730, 128/203.28, 205.17; 272/99 R; 92/43, 44; 73/262

[56] References Cited

U.S. PATENT DOCUMENTS

| | | | |
|---|---|---|---|
| 513,924 | 1/1894 | Hartnett | 128/203.28 |
| 3,363,260 | 1/1968 | Garbe | 128/728 |
| 3,754,546 | 8/1973 | Cooper | 128/727 |
| 4,096,855 | 6/1978 | Fleury, Jr. | 128/727 |
| 4,114,608 | 9/1978 | Russo | 128/725 |
| 4,241,740 | 12/1980 | Brown | 128/728 |

FOREIGN PATENT DOCUMENTS 27154 4/1981 European Pat. Off. ............ 128/728

Primary Examiner—Henry J. Recla

[57] ABSTRACT

A volume type lung exerciser consisting of a light bellows made of a stack of flat sheets of plastic film welded together and having an inner support skeleton of semi-rigid sheets. The bellows is hung from a collapsible leg stand which slides into a movable platform to limit the bellows extension. The platform is in the form of a shallow box which can accept the folded assembly for storage.

6 Claims, 3 Drawing Figures

U.S. Patent     Aug. 24, 1982     4,345,605

LUNG EXERCISER

FIELD OF INVENTION

Surgery

OBJECTS

Patients with severe illness or those having been operated on recently are often weak to the point where they find it difficult to breath deeply. The human lung is a labyrinth of passages that get increasingly smaller deeper into the lung. If the small passages are not used at least occasionally over a period of time, they tend to clog and could atrophy. A normally healthy person will sigh or yawn on a fairly regular basis which exercises the small passages of the lungs. Deep breathing exercises or activities that require heavy breathing, such as running, are good for the lungs.

Since lung problems with inactive patients are a well known phenomenon, therapists have for some time used various devices to get the patient to use or redevelop their lungs. Among these are blow bottles which require a patient to blow water out of a bottle, ball type flowmeters which force a patient to draw or expire breath at a higher than normal rate, and volume related devices that measure the vital capacity of the lung and encourage deep breathing. There are also a number of positive pressure devices which force pressure into the lungs to expand them with the patient being passive.

The volume related devices that require a patient to inhale a set amount of air and repeat the exercise a number of times are currently the most popular. Generally they are a collapsible container with a calibrated, preset and adjustable volume that the patient must displace by inhaling 10 to 20 times a treatment. Bellows are commonly used as are folding bags and boxes. It is important that the container offer as little resistance as possible when being emptied since it is the inhaled displacement of volume that is important and not the force needed to do it. Some bellows are so stiff that when the required volume is taken from them they have such a memory for their original shape that they create a negative pressure. More expensive or elaborate devices use counterweights or float a chamber in water to eliminate weight or negative pressure. Electronic devices coupled to flow meters can do the job very well.

What is proposed here is a simple, inexpensive device that can be readily understood and used and can be thrown away after one patient uses it. Materials used are common in both manufacturing and in hospital use. The design offers the therapist the opportunity to prescribe varied treatments to suit the patient.

When designing a disposable device it is important to use inexpensive materials and as little material as possible. It also must be possible to assemble the unit with a small amount of labor or machine time. A bellows to enclose a given volume (4 liters for example) could be made of rubber in a dip molding, or plastic in a blow molding. Welded bellows made of sheet plastic also can be used.

One of the cheapest ways to enclose a volume is with a plastic bag. Plastic such as polyethylene can be easily extruded into sheet or tubing and readily welded into a closed shape. If a series of sealed bags are stacked and sealed together near their center with interconnecting holes a bellows can be made.

If the volume of a bellows is known, a breathing tube or hose can be connected to it and a patient instructed to collapse the bellows by inhaling. It is best to have a stand to control the bellows and also to allow it to be adjustable as to volume.

Polyethylene bags with a thickness of 0.001 to 0.002 inch have adequate strength to hold positive or negative pressure in small amounts and are easily sealed to other materials and other thicknesses may be used. When negative pressure is applied inside a bellows made of thin polyethylene bags, the bellows tends to collapse from the sides rather than the bottom. The bellows should collapse from the bottom to make calibration practical. To prevent side collapse a series of cards (one in each layer) can be added. These cards (which may be cardboard or semi-rigid plastic) must be sized slightly smaller than the inside of the bag to allow the sides to come in a little when the bellows extends.

The U-shaped support from which the bellows hangs can be made of inexpensive cardboard or rigid plastic. Graduations representing the volume of the bellows can be printed or labeled on the sides. If the support is sized to fit into a tray or box top and the tray can be slid up and down, the bellows can be volume sized for different patients.

If the U-shaped support is made of corrugated cardboard and the top card in the bellows also is, the output fitting can be snap fitted into a common hole in the two and used to hold the assembly together. Corrugated cardboard is easily scored and bent and can be folded flat with the bellows collapsed inside. The bottom movable tray can be used to hold the collapsed assembly and with the addition of a box top or a cover sleeve, the assembly is packaged. The bottom box or tray can be made from a common box design that folds together. With the addition of two slots the box will work as the movable support. Either or both the box and the hanger could be made of other materials such as thermoformed plastic.

As with any exercise, counting the number of times the exercise is done is important. If the output connection is an elbow with a cleanout cap (making the elbow a tee) a means for getting to the moving bellows to sense the cycles is provided.

These and other objects will be apparent from the following specification and drawings in which:

FIG. One shows a plan view of the bellows portion of the device.

FIG. Two is a perspective view of the entire assembly.

FIG. Three is a perspective view of the bottom tray of the device.

Referring now to the drawings, in which like reference numerals denote similar elements, FIG. One shows a bellows 2 formed by welding together a series of six plastic bags 4, said plastic bags being two sheets of plastic closed around all four outer edges. The weld area 3 may be made by heat sealing, adhesive bonding or other suitable means and is shaped as a band around an unsealed area. Within the unsealed area a hole is cut to interconnect the inner air space of each of the layers or bags 4. The interconnecting hole shall be large enough to allow any air passed through top port 5 in either direction to move without restriction in volumes associated with breathing. A top fitting 5 of 22 mm diameter is a commonly accepted breathing tube connector. The top fitting 5 is attached to the top layer by suitable means such as heat sealing, adhesive bonding or by snap fitting into a flange ring or sheet provided inside the top bag. Each bag 4 becomes an element or layer of a belows. Said bellows could be any number of layers suited to the end use.

Using the thinnest practical material for bags 4 to save cost will result in a bellows that is too flexible to withstand even a slight vacuum. Instead of the bottom of the bellows moving up and down, the sides will fold in. To prevent this, support cards or inserts 6 may be added. These cards are simple sheets of a semi-rigid material such as cardboard, plastic sheet or heavy paper and are cut with a small clearance fit to the bag 4. Without a clearance the layers would be stretched tight when the bellows was folded and the bellows could not extend. The amount of clearance controls the maximum extension of the bellows. The weight of the cards 6 adds to the weight of the assembly 2 and governs how quickly the bellows expands upon release after having been drawn up by an inhaling patient.

Each card 6 except the lowest or bottom card must have a center hole at least as large as the hole between layers to allow free passage of air. The lowest card 6 could also be heavier to improve the smooth working of the bellows by makng the bellows expand bottom first.

Given the bellows assembly 2 of FIG. One, it is necessary to provide a means of hanging or supporting the bellows so it can be easily used. In FIG. Two where the entire assembly is referenced generally by 7 the bellows assembly 2 is shown installed in a U-shaped hanger 8 and suspended by fitting 5. Hanger 8 could be made of semi-rigid material such as fluted cardboard or thin plastic. Fitting 5 has a suitable barb or fitting to allow it to be caught by a hole in hanger 8.

Hanger 8 is made narrower than bellows assembly 2 so that the bellows 2 is easily seen from any angle. By putting calibrations on the upright sides of hanger 8, as the bellows 2 contracted, the bottom most layer would be used as an indicator of the volume left in the bellows or the volume displaced by the inhaler.

A tray 9 is shown at the bottom of assembly 7 which serves to hold the open end of the hanger 8 in place. The tray 9 has the form of a shallow box open on one side. The closed side of tray 9 may be placed either up or down in the assembly depending on the volume or space needed. The tray 9 would have slots 10 corresponding to the width of the legs of hanger 8 which would allow the tray 9 to be slid up and down the hanger 8 further adjusting the volume limit of bellows assembly 2. This adjustment would be necessary to allow the therapist to adjust the treatment to the patient's needs.

The tray 9 could be a simple vacuum formed plastic box or preferably a folded cardboard box. Making cardboard boxes by die cutting, scoring and folding is commonly done. If the tray 9 is formed by folding a single sheet as shown in FIG. Three, two sides 11 are folded double thickness around two tabs tucked in from the remaining sides of the tray. Most often a slot 10 is provided in the bottom of the tray to accept a tab 12 sticking out of side 11 to allow the assembly to be locked together. In the present design the slots 10 are made somewhat wider in the narrower dimension so an extra layer of material could be slid through. A corresponding slot 13 is cut at the opposite edge of the fold on the open side of the tray so the leg of hanger 8 can slide all the way through.

Tray 9 is made large enough in all dimensions so the bellows 2 can be contracted, the legs of hanger 8 folded inward over each other and bellows 2 and the entire assembly fitted into the tray. Since fitting 5 takes more height than the rest of the assembly 7 a space will be left into which accessories such as connecting tubing can be fitted. The entire assembly of folded bellows 2 with hanger 8 in tray 9 can be covered with a sleeve, bag, or sheet of material to form a closed package.

Fitting 5 could be anchored firmly to bellows 2 or if it is snapped in, may be allowed to swivel. The swivel action would be a preferred feature. If an elbow shape is used for fitting 5, it would be easy to provide a port 14 at the bend that would be normally closed by a cap or plug. This passageway or port could be used to reach the inside of the bellows 2 particularly to the bottom layer so a counter or indicator could be provided to indicate the bellows had been completely emptied.

To make use of the device the therapist or patient would open the package and remove the hanger bellows assembly. The legs of hanger 8 should fall open and the bellows 2 extend itself. The legs of hanger 8 would be inserted through the slots 10 and 13 in tray 9. The choice of whether the open side of tray 9 was up or down would depend on the calibration or on the maximum volume desired. With the open side of tray 9 up towards the bellows, the maximum volume would be greater than the case with the closed side up by an amount proportional to the greater distance the bellows can travel. The tray 9 would be positioned up or down on the hanger 8 to set the maximum volume desired for bellows 2 according to the calibrations provided on hanger 8.

A breathing tube would be connected to fitting 5 so the patient could put the opposite end in his mouth (with the addition of a mouth piece) and communicate with the interior of bellows 2. To exercise, the patient would try by sucking air out of the breathing tube attached to the fitting 5, to empty the bellows completely. The therapist or physician would prescribe the number of times the exercise should be done and to what volume.

I claim:

1. A device to provide volume exercise for a patients lungs said device comprising a lightweight bellows made up of a plurality of vertically spaced pairs of square layers of plastic film, each pair of layers being joined at their peripheral edge, each layer having an opening at the center thereof, the peripheral edge of one of said openings on each layer of said pairs of layers being sealed to the peripheral edge of an opening on an adjacent layer of an adjacent pair of said layers, said openings in each layer defining an interconnecting passage between each pair of layers, a solid bottom layer sealed to the peripheral edge of the lowermost layer of said pair of layers, a top layer sealed to the peripheral edge of the uppermost layer of said pair of layers, said uppermost layer having an outlet opening therein, whereby a closed volume is formed with a passage out the upper most layer and being readily collapsible with very little resistance to collapse due to the lightweight and high flexibility said bellows an outlet fitting connected to said outlet opening adapted to be connected to tubing and thereby allow a patient to exercise by drawing air from the bellows into the lungs, the maximum volume capacity of said closed volume being greater than the amount, and means to reduce the volume of said bellows by partially collapsing the bellows or limiting its extension including a support system for the bellows, said support system comprising a foldable hanger in the shape of an inverted U having its bridge section connected to the outlet fitting and its legs extending downwardly on opposite sides of said bellows, the distance the bellows could extend being directly related to the volume in the bellows, a movable platform slidably mounted to each leg of said hanger adjacent the lowermost layer of said bellows wherein the extension of said bellows is limited in an adjustable fashion by a movable platform into which the legs of the U shaped hanger could slide, the position of the platform up or down the hanger being calibrated to bellows volume for prescribed lung volume exercise, said platform being an open top shallow box with opposing slots in which the legs of the hanger slide, wherein said box could act as a storage container for the collapsed bellows and folded hanger when not in use, the bellows further being provided with a skeleton made up of flat sheets of semi-rigid material, each sheet having a hole at the center for air flow and being inserted into each pair of layers of the bellows, whereby the bellows, when evacuated, will reduce in volume by the bottom moving up rather than having the sides cave in, said size of said sheets being also a free extension limit by limiting the amount the bottom could drop since the sides must move in a certain amount to have the bottom and top move apart.

2. A bellows type lung exerciser as in claim 1, wherein said pairs of layers of said bellows made by stacking and sealing interconnected thin plastic pillows or bags of square or other shape, each bag containing a piece of flat semi-rigid material to maintain an expanded horizontal shape when said bellows is empty of air and contracted vertically.

3. A lung exerciser as in claim 1, wherein said U-shaped hanger, semi-rigid flat material is sized to partially or fully enclose the extended bellows on the top and two sides, said support may be folded flat with the collapsed bellows within, said hanger having a at the top to allow said outlet fitting to pass through which fitting may also provide the means to hold the bellows assembly to the hanger.

4. A lung exerciser as in claim 1 wherein said uppermost layer includes a flat sheet of semi-rigid material having a hole therein into which is connected said outlet fitting, said outlet fitting being provided with suitable barbs to lock the assembly together.

5. A lung exerciser assembly as in claim 1 wherein said outlet fitting includes a first laterally extending port being sized to fit common breathing tubing or other patient connecting means and an additional port extending parallel to the longitudinal axis of said bellows providing a passage to the inside of the bellows assembly to make it accessible for a counter to contact the moving bellows.

6. A lung exerciser as in claim 1 having little resistance to volume changes due to its low weight and extreme flexibility and thereby being truly a volume measurement device rather than a spring force for the patient to overcome or deal with at the end of each stroke.

* * * * *